United States Patent [19]
Höök et al.

[11] Patent Number: 5,840,846
[45] Date of Patent: *Nov. 24, 1998

[54] FIBRONECTIN BINDING PROTEIN AS WELL AS ITS PREPARATION

[75] Inventors: Magnus Höök, Birmingham, Ala.; Klas Jönsson; Kjell Martin Lindberg, both of Upsala, Sweden; Christer Signäs, Upsala, Sweden

[73] Assignee: Alfa-Laval Agri International Aktiebolag, Tumba, Sweden

[ * ] Notice: The term of this patent shall not extend beyond the expiration date of Pat. No. 5,652,217.

[21] Appl. No.: 725,492

[22] Filed: Oct. 4, 1996

Related U.S. Application Data

[62] Division of Ser. No. 340,458, Nov. 14, 1994, Pat. No. 5,320,951, which is a continuation of Ser. No. 974,181, Nov. 10, 1992, abandoned, which is a division of Ser. No. 520,808, May 9, 1990, Pat. No. 5,175,096.

[30] Foreign Application Priority Data

May 11, 1989 [SE] Sweden .................................. 8901687

[51] Int. Cl.⁶ ............................. C07K 14/00; C07K 14/31
[52] U.S. Cl. ........................... 530/350; 530/42; 530/413; 530/416; 530/334; 530/825; 130/200; 435/69.7; 435/320.1; 435/172.3; 435/252.3; 435/252.33; 536/23.7

[58] Field of Search ................................. 435/172.3, 320.1, 435/252.3, 252.33, 69.7; 536/23.7; 935/9, 10, 11, 16, 22, 29, 72, 73; 930/200; 530/350, 412, 413, 416, 825, 334

[56] References Cited

U.S. PATENT DOCUMENTS

| | | | |
|---|---|---|---|
| 5,320,951 | 6/1994 | Hook et al. | 435/69.1 |
| 5,571,514 | 11/1996 | Hook et al. | 424/190.1 |
| 5,652,217 | 7/1997 | Hook et al. | 514/12 |

OTHER PUBLICATIONS

Watson et al. 1987 in: Molecular Biology of The Gene, fourth edition, Benjamin/Cummings Publ. Co., Inc., Menlo Park, CA, p. 313.

Flock et al. 1987 EMBO J. 6(8):2351–2357.

*Primary Examiner*—Christopher S.F. Low
*Attorney, Agent, or Firm*—Burns, Doane, Swecker & Mathis, L.L.P.

[57] ABSTRACT

The present invention relates to a new recombinant hybrid-DNA-molecule comprising a nucleotide sequence from *S. aureus* coding for a protein, or polypeptide, having fibronectin binding properties.

8 Claims, 8 Drawing Sheets

FIG. 1A

```
  1 GTTAACAACA ATCTTAAACTT TTTATTAACT CGCTTTTTTT CATTGCTTTT
 51 AAAAACCGAA CAATATAGAA TTGCATTTAT TGAGTTTTTA AAATAAATGA
101 ATTTTGCATT TAAGGGAGAA TATTATAGTG AAAAGCAATC TTAGATACGG
151 CATAAGAAAA CACAAATTGG GAGCGGCCTC AGTATTCTTA GGAACAATGA
201 TCGTTGTTGG AATGGGACAA GAAAAAGAAG CTGCAGCATC GGAACAAAAC
251 AATACTACAG TAGAGGAAAG TGGGAGTTCA GCTACTGAAA GTAAAGCAAG
301 CGAAACACAA ACAACTACAA ATAACGTTAA TACAATAGAT GAAACACAAT
351 CATACAGCGC GACATCAACT GAGCAACCAT CACAATCAAC ACAAGTAACA
401 ACAGAAGAAG CACCGAAAAC TGTGCAAGCA CCAAAAGTAG AAACTTCGCG
451 AGTTGATTTG CCATCGGAAA AAGTTGCTGA TAAGGAAACT ACAGGAACTC
501 AAGTTGACAT AGCTCAACAA AGTAAAGTCT CAGAAATTAA ACCAAGAATG
551 AAAAGATCAA CTGACGTTAC AGCAGTTGCA GAGAAAGAAG TAGTGGAAGA
601 AACTAAAGCG ACAGGTACAG ATGTAACAAA TAAAGTGGAA GTATAAGAAG
651 GTAGTGAAAT TGTAGGACAT AAACAAGATA CGAATGTTGT AAATCCTCAT
701 AACGCAGAAA GAGTAACCTT GAAATATAAA TGGAAATTTG GAGAAGGAAT
751 TAAGGCGGGA GATTATTTTG ATTTCACATT AAGCGATAAT GTTGAAACTC
801 ATGGTATCTC AACACTGCGT AAAGTTCCGG AGATAAAAAG TACAGATGGT
851 CAAGTTATGG CGACAGGAGA AATAATTGGA GAAAGAAAAG TTAACTGCTT
901 GTTTAAAGAA TATGTACAAG AAAAGAAAGA TTTAACTGCT GAATTATCTT
951 TAAATCTATT TATTGATCCT ACAACAGTGA CGCAAAAAGG TAACCAAAAT
```

FIG. 1B

```
1001  GTTGAAGTTA  AATTGGGTGA  GACTACGGTT  AGCAAAATAT  TTAATATTCA
1051  ATATTTAGGT  GGAGTTAGAG  ATAATTGGGG  AGTAACAGCT  AATGGTCGAA
1101  TTGATACTTT  AAATAAAGTA  GATGGGAAAT  TTAGTCATTT  TGCGTACATG
1151  AAACCTAACA  ACCAGTCGTT  AAGCTCTGTG  ACAGTAACTG  GTCAAGTAAC
1201  TAAAGGAAAT  AAACCAGGGG  TTAATAATCC  AACAGTTAAG  GTATATAAAC
1251  ACATTGGTTC  AGACGATTTA  GCTGAAAGCG  TATATGCAAA  GCTTGATGAT
1301  GTCAGCAAAT  TTGAAGATGT  GACTGATAAT  ATGAGTTTAG  ATTTTGATAC
1351  TAATGGTGGT  TATTCTTTAA  ACTTTAATAA  TTTAGACCAA  AGTAAAAATT
1401  ATGTAATAAA  ATATGAAGGG  TATTATGATT  CAAATGCTAG  CAACTTAGAA
1451  TTTCAAACAC  ACCTTTTTGG  ATATTATAAC  TATTATTATA  CAAGTAATTT
1501  AACTTGGAAA  AATGGCGTTG  CATTTTACTC  TAATAACGCT  CAAGGCGGACG
1551  GCAAAGATAA  ACTAAAGGAA  CCTATTATAG  AACATAGTAC  TCCTATCGAA
1601  CTTGAATTTA  AATCAGAGCC  GCCAGTGGAG  AAGCATGAAT  TGACTGGTAC
1651  AATCGAAGAA  AGTAATGATT  CTAAGCCAAT  TGATTTTGAA  TATCATACAG
1701  CTGTTGAAGG  TGCAGAAGGT  CATGCAGAAG  GTACCATTGA  AACTGAAGAA
1751  GATTCTATTC  ATGTAGACTT  TGAAGAATCG  ACACATGAAA  ATTCAAAACA
1801  TCATGCTGAT  GTTGTTGAAT  ATGAAGAAGA  TACAAACCCA  GGTGGTGGTC
1851  AGGTTACTAC  TGAGTCTAAC  CTAGTTGAAT  TTGACGAAGA  TTCTACAAAA
1901  GGTATTGTAA  CTGGTGCTGT  TAGCGATCAT  ACAACAATTG  AAGATACGAA
1951  AGAATATACG  ACTGAAAGTA  ACTTGATTGA  ACTAGTAGAT  GAACTACCTG
```

FIG. 1C

```
2001 AAGAACATGG TCAAGCGCAA GGACCAATCG AGGAAATTAC TGAAAACAAT
2051 CATCATATTT CTCATTCTGG TTTAGGAACT GAAAATGGTC ACGGTAATTA
2101 TGGCGTGATT GAAGAAATCG AAGAAAATAG CCACGTGGAT ATTAAGAGTG
2151 AATTAGGTTA CGAAGGTGGC CAAAATAGCG GTAATCAGTC ATTTGAGGAA
2201 GACACAGAAG AAGATAAACC GAAATATGAA CAAGGTGGCA ATATCGTAGA
2251 TATCGATTTC GATAGTGTAC CTCAAATTCA TGGTCAAAAT AATGGTAACC
2301 AATCATTCGA AGAAGATACA GAGAAAGACA AACCTAAGTA TGAACAAGGT
2351 GGTAATATCA TTGATATCGA CTTCGACAGT GTGCCACATA TTCACGGATT
2401 CAATAAGCAC ACTGAAATTA TTGAAGAAGA TACAAATAAA GATAAACCAA
2451 ATTATCAATT CGGTGGACAC AATAGTGTTG ACTTTGAAGA AGATACACTT
2501 CCACAAGTAA GTGGTCATAA TGAAGGTCAA CAAACGATTG AAGAAGATAC
2551 AACACCTCCA ATCGTGCCAC CAACGCCACC GACACCAGAA GTACCAAGCG
2601 AGCCGGAAAC ACCAACACCA CCGACACCAG AAGTACCAAG CGAGCCGGAA
2651 ACACCAACAC CGCCAACGCC AGAGGTACCA ACTGAACCTG GTAAACCAAT
2701 ACCACCTGCT AAAGAAGAAC CTAAAAAACC TTCTAAACCA GTGGAACAAG
2751 GTAAAGTAGT AACACCTGTT ATTGAAATCA ATGAAAAGGT TAAAGCAGTG
2801 GTACCAACTA AAAAAGCACA ATCTAAGAAA TCTGAACTAC CTGAAACAGG
2851 TGGAGAAGAA TCAACAAACA ACGGCATGTT GTTCGGCGGA TTATTTAGCA
2901 TTTTAGGTTT AGCGTTATTA CGCAGAAATA AAAGAATCA CAAAGCATAA
2951 TCAATCCAAA ATTGACAGGT TTATTTCATA AATTATATGA AGTAAGCCTG
```

```
3001  TTTTTTAAAA  TTAAAACAAA  TTTCCCAAGA  AATAATTACA  TACTCAATGA
3051  CACTATGAAG  GCGTTCTAAT  TAGTGTTAAA  ATGACGTTGA  TACATAGATT
3101  TAATACTTAG  GAAAAGGAGC  ACATTAACTT  TGAAAAAAAT  AAAAAGGCA
3151  ATCATTCCCG  CTGCTGGTTT  AGGGACTAGA  TTTTTACCAG  CAACTAAAGC
3201  GATGCCAAAG  GAAATGCTTC  CTATCTTAGA  TAAACCCACA  ATACAATATA
3251  TCGTTGAAGA  AGCTGCAAGA  GCTGGAATTG  AAGATATTAT  TATAGTGACA
3301  GGTCGCCACA  AACGCGCGAT  TGAAGATCAT  TTTGATAGTC  AAAAAGAATT
3351  AGAAATGGTG  TTAAAAGAAA  AAGGTAAATC  TGAATTACTA  GAGAAAGTTC
3401  AGTATTCAAC  GGAACTTGCG  AATATTTTTT  ATGTAAGGCA  GAAAGAACAA
3451  AAAGGTTTAG  GGCATGC
```

LGTENGHGNYDVIEEIEENSHVD—IKSELGYEGGQNSGNQSFEEDTEEDKPKYEQGGNIVD
——————————————————————————————————————————————————————————————
LGTENGHGNYGVIEEIEENSHVD—IKSELGYEGGQNSGNQSFEEDTEEDKPKYEQGGNIVD

IDFDSVPQIHGQNKGNQSFEEDTEKDKPKYEHGGNII-DIDFDSVPHIHGFNKHTEIIEED
——————————————————————————————————————————————————————————————
IDFDSVPQIHGQNNGNQSFEEDTEKDKPKYEQGGNII-DIDFDSVPHIHGFNKHTEIIEED

TNKDKPSYQFGGHNSVDFEEDTLPKVSGQNEGQQTIEEDTTPPIVPPTPEVPSEPET
——————————————————————————————————————————————————————————
TNKDKPNYQFGGHNSVDFEEDTLPQVSGHNEGQQTIEEDTTPPIVP···········

PTPPTPEVPSEPETPTPPTPEVPAEPGKPVPPAKEEPKKPSKPVEQ
——————————————————————————————————————————————
PTPPTPEVPSEPETPTPPTPEVPTEPGKPIPPAKEEPKKPSKPVEQ

GKVVTPVIEINEKVKAVAPTKKPQSKKSELPETGGEESTNKGMLFGGLFSILGLALLRRN
——————————————————————————————————————————————————————————————
GKVVTPVIEINEKVKAVVPTKKAQSKKSELPETGGEESTNNGMLFGGLFSILGLALLRRN

KKNHKA
——————
KKNHKA
```

```
  1  VKSNLRYGIR  KHKLGAASVF  LGTMIVVGMG  QEKEAAASEQ  NNTTVEESGS
 51  SATESKASET  QTTTNNVNTI  DETQSYSATS  TEQPSQSTQV  TEEAPKTVO
101  APKVETSRVD  LPSEKVADKE  TTGTQVDIAQ  QSKVSEIKPR  MKRSTDVTAV
151  AEKEVVEETK  ATGTDVTNKV  EVEEGSEIVG  HKQDTNVVNP  HNAERVTLKY
201  KWKFGEGIKA  GDYFDFTLSD  NVETHGISTL  RKVPEIKSTD  GQVMATGEII
251  GERKVRYTFK  EYVQEKKDLT  AELSLNLFID  PTTVTQKGNQ  NVEVKLGETT
301  VSKIFNIQYL  GGVRDNWGVT  ANGRIDTLNK  VDGKFSHFAY  MKPNNQSLSS
351  VTVTGQVTKG  NKPGVNNPTV  KVYKHIGSDD  LAESVYAKLD  DVSKFEDVTD
401  NMSLDFDTNG  GYSLNFNNLD  QSKNYVIKYE  GYYDSNASNL  EFQTHLFGYY
451  NYYYTSNLTW  KNGVAFYSNN  AQGDGKDKLK  EPIIEHSTPI  ELEFKSEPPV
501  EKHELTGTIE  ESNDSKPIDF  EYHTAVEGAE  GHAEGTIETE  EDSIHVDFEE
551  STHENSKHHA  DVVEYEEDTN  PGGGQVTES  NLVEFDEDST  KGIVTGAVSD
601  HTTIEDTKEY  TTESNLIELV  DELPEEHGQA  QGPIEEITEN  NHHISHSGLG
651  TENGHGNYGV  IEEIEENSHV  DIKSELGYEG  GQNSGNQSFE  EDTEEDKPKY
701  EQGGNIVDID  FDSVPQIHGQ  NNGNQSFEED  TEKDKPKYEQ  GGNIIDIDFD
751  SVPHIHGFNK  HTEIIEEDTN  KDKPNYQFGG  HNSVDFEEDT  LPQVSGHNEG
801  QQTIEEDTTP  PIVPPTPPTP  EVPSEPETPT  PPTPEVPSEP  ETPTPPTPEV
851  PTEPGKPIPP  AKEEPKKPSK  EVPQGKVVTP  PVEQGKVVTP  VVPTKKAQSK
901  KSELPETGGE  ESTNNGMLFG  GLFSILGLAL  LRRNKKNHKA
```

… 5,840,846

FIBRONECTIN BINDING PROTEIN AS WELL AS ITS PREPARATION

This application is a divisional of application Ser. No. 08/340,458, filed Nov. 14, 1994, U.S. Pat. No. 5,320,951 which is a continuation of Ser. No. 07/974,181, filed Nov. 10, 1992, now abandoned which is a divisional of Ser. No. 07/520,808, filed May 9, 1990, now issued as U.S. Pat. No. 5,175,096.

TECHNICAL FIELD

The present invention relates to a fibronectin binding protein as well as hybrid-DNA-molecules, e.g. plasmids or phages comprising a nucleotide sequence coding for said protein. Further the invention relates to microorganisms comprising said molecules and their use producing said protein, as well as the synthetic preparation of said protein.

The object of the present invention is to obtain a minimal fibronectin binding protein.

A further object is to obtain said protein by means of a genetic engineering technique by using e.g. a plasmid comprising a nucleotide sequence coding for said protein.

A further object is to obtain a possibility of preparing said protein by chemical synthesis.

Further objects will be apparent from the following description.

BACKGROUND OF THE INVENTION

WO-A1-85/05553 discloses bacterial cell surface proteins having fibronectin, fibrinogen, collagen, and/or laminin binding ability. Thereby it is shown that different bacteria have an ability to bind to fibronectin, fibrinogen, collagen, and/or laminin. It is further shown that fibronectin binding protein has a molecular weight of 165 kD and/or 87 kD, whereby it is probable that the smaller protein is a part of the larger one.

Fibronectin is a large glycoprotein ($M_r$ ca 450 kd) with two similar subunits, which may vary in molecular size depending on a complex splicing pattern of a precursor mRNA (1). The major function of fibronectin, which is found in body fluids, blood clots and extracellular matrices, seems to be related to the ability of the protein to mediate substrate adhesion of most eukaryotic cells (2, 3, 4, 5.)

In the late seventies, Kuusela found that fibronectin not only interacts with eucaryotic cells but also binds to cells of *Staphylococcus aureus* (6). Since this observation, a number of pathogenic microorganisms have been shown to bind to fibronectin with a high degree of specificity and a high affinity, such as streptococci (group A, C, and G), coagulase negative staphylococci, *E. coli* and *Treponema pallidum*. Fibronectin in the extracellular matrix appears to serve as a substratum also for the adhesion of different microorganisms. The binding of fibronectin may for some microorganisms represent a crucial step in the colonization of host tissue and development of infection.

Several different cell surface components have been implicated as fibronectin receptors on Gram-positive bacteria including lipotechioc acid (8, 9) and protein (10). In previous studies a fibronectin binding protein with a $M_r$ of 197–210 kD has been isolated from *S. aureus* strain Newman (11, 12) and tentatively identified as a fibronectin receptor. The binding site in fibronectin for eukaryotic cells has been localized to a tetrapeptide (ArgGlyAspSer) in the central portion of each of the two subunits forming the fibronectin, which is different to the binding site of most bacteria so far studied. The bacteria appear to bind to the aminoterminal 29 kDa domain of the fibronectin subunit.

An eukaryotic receptor has been identified as a 140 kDa complex in the cell membrane, whereas the bacterial fibronectin binding protein (FNBP) of *Staphylococcus aureus* strain Newman has been identified as a 210 kDa protein. From previous studies (SE-A-8702272-9) it has been reported of the cloning, expression and the complete nucleotide sequence of a gene (herein called gene 1) for a FNBP in *Staphylococcus aureus*.

In the present application the cloning, expresssion and the nucleotide sequence of a further gene, gene 2, located downstream the previous studied and reported fibronectin binding protein sequence. To further characterize this fibronectin binding protein from *S aureus*, the gene for this protein has been cloned in *E. coli*. The fibronectin binding domain within this protein has also been localized.

BRIEF DESCRIPTION OF THE DRAWINGS

FIGS. 1A to 1D depict the nucleotide sequence of the nucleic acid encoding the fibronectin binding protein.

FIG. 2 presents a comparison between the amino acid sequences of the fibronectin binding proteins encoded by gene 1 and gene 2, respectively, which are given in parallel.

FIG. 4 is the deduced amino acid sequence of the cloned fnbB from *S. aureus* strain 8325-4.

DESCRIPTION OF THE INVENTION

Figure 3:
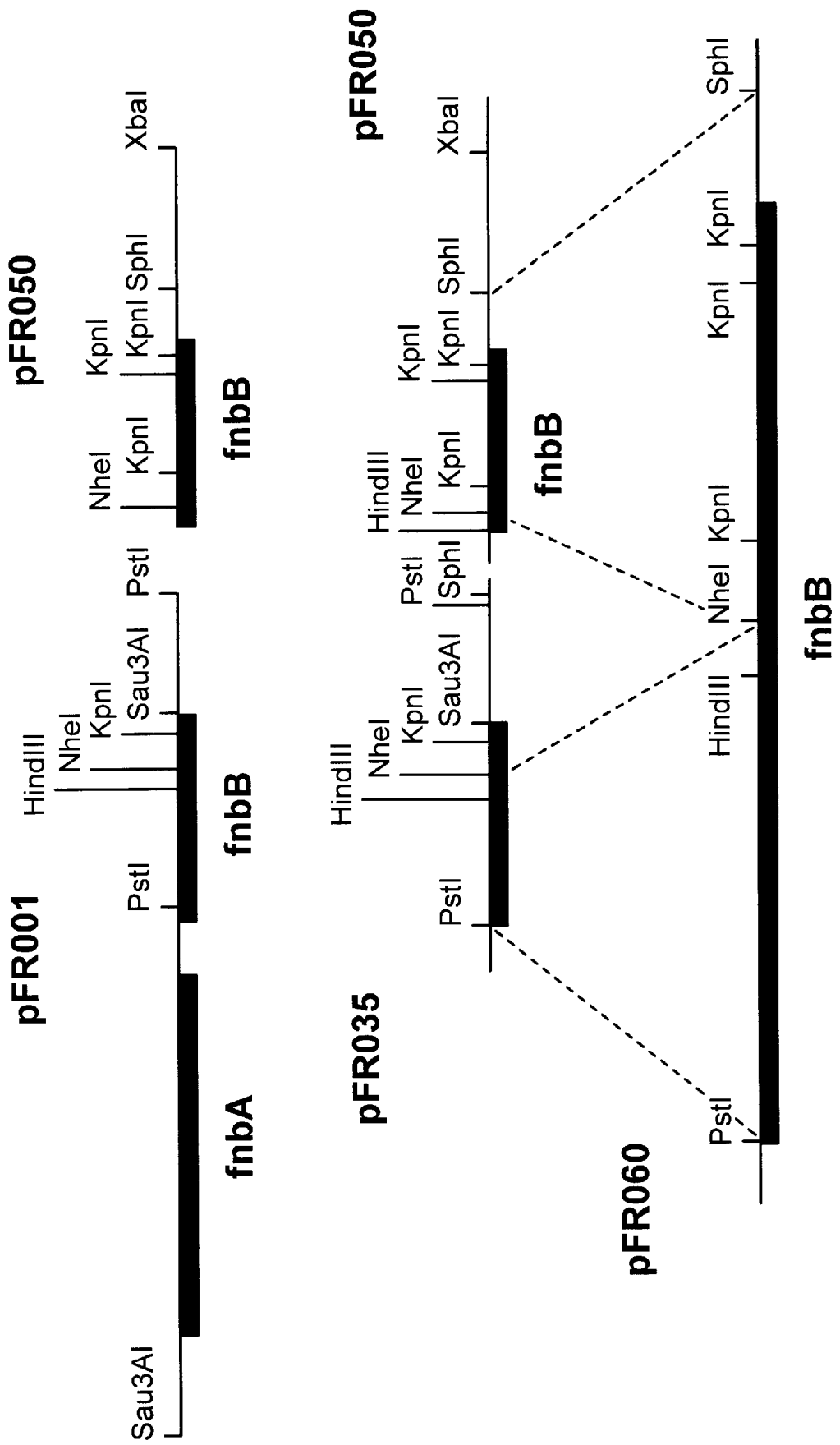
FIG. 3 is a restriction map of the original clones pFR0001 and pFR050 together with subclones pFR035 and pFR036. The location of fnbA and fnbB is indicated. The sequenced fragment of the insert is shown in more detail. The coding sequences in each clone are shown with bold lines.

It has now surprisingly been found possible to obtain a hybride-DNA-molecule comprising a nucleotide sequence coding for a protein or a polypeptide having fibronectin binding properties. As evident from below the following nucleotide sequence is present in the gene coding for said protein:

```
GTTAACAACA ATCTTAACTT TTTATTAACT CGCTTTTTTT CATTGCTTTT

AAAAACCGAA CAATATAGAA TTGCATTTAT TGAGTTTTTA AAATAAATGA

ATTTTGCATT TAAGGGAGAA TATTATAGTG AAAAGCAATC TTAGATACGG

CATAAGAAAA CACAAATTGG GAGCGGCCTC AGTATTCTTA GGAACAATGA
```

```
-continued
TCGTTGTTGG AATGGGACAA GAAAAAGAAG CTGCAGCATC GGAACAAAAC

AATACTACAG TAGAGGAAAG TGGGAGTTCA GCTACTGAAA GTAAAGCAAG

CGAAACACAA ACAACTACAA ATAACGTTAA TACAATAGAT GAAACACAAT

CATACAGCGC GACATCAACT GAGCAACCAT CACAATCAAC ACAAGTAACA

ACAGAAGAAG CACCGAAAAC TGTGCAAGCA CCAAAAGTAG AAACTTCGCG

AGTTGATTTG CCATCGGAAA AAGTTGCTGA TAAGGAAACT ACAGGAACTC

AAGTTGACAT AGCTCAACAA AGTAAAGTCT CAGAAATTAA ACCAAGAATG

AAAAGATCAA CTGACGTTAC AGCAGTTGCA GAGAAAGAAG TAGTGGAAGA

AACTAAAGCG ACAGGTACAG ATGTAACAAA TAAAGTGGAA GTAGAAGAAG

GTAGTGAAAT TGTAGGACAT AAACAAGATA CGAATGTTGT AAATCCTCAT

AACGCAGAAA GAGTAACCTT GAAATATAAA TGGAAATTTG GAGAAGGAAT

TAAGGCGGGA GATTATTTTG ATTTCACATT AAGCGATAAT GTTGAAACTC

ATGGTATCTC AACACTGCGT AAAGTTCCGG AGATAAAAAG TACAGATGGT

CAAGTTATGG CGACAGGAGA AATAATTGGA GAAAGAAAAG TTAGATATAC

GTTTAAAGAA TATGTACAAG AAAAGAAAGA TTTAACTGCT GAATTATCTT

TAAATCTATT TATTGATCCT ACAACAGTGA CGCAAAAAGG TAACCAAAAT

GTTGAAGTTA AATTGGGTGA GACTACGGTT AGCAAAATAT TTAATATTCA

ATATTTAGGT GGAGTTAGAG ATAATTGGGG AGTAACAGCT AATGGTCGAA

TTGATACTTT AAATAAAGTA GATGGGAAAT TTAGTCATTT TGCGTACATG

AAACCTAACA ACCAGTCGTT AAGCTCTGTG ACAGTAACTG GTCAAGTAAC

TAAAGGAAAT AAACCAGGGG TTAATAATCC AACAGTTAAG GTATATAAAC

ACATTGGTTC AGACGATTTA GCTGAAAGCG TATATGCAAA GCTTGATGAT

GTCAGCAAAT TTGAAGATGT GACTGATAAT ATGAGTTTG  ATTTTGATAC

TAATGGTGGT TATTCTTTAA ACTTTAATAA TTTAGACCAA AGTAAAAATT

ATGTAATAAA ATATGAAGGG TATTATGATT CAAATGCTAG CAACTTAGAA

TTTCAAACAC ACCTTTTTGG ATATTATAAC TATTATTATA CAAGTAATTT

AACTTGGAAA AATGGCGTTG CATTTTACTC TAATAACGCT CAAGGCGACG

GCAAAGATAA ACTAAAGGAA CCTATTATAG AACATAGTAC TCCTATCGAA
```

-continued

```
CTTGAATTTA AATCAGAGCC GCCAGTGGAG AAGCATGAAT TGACTGGTAC

AATCGAAGAA AGTAATGATT CTAAGCCAAT TGATTTTGAA TATCATACAG

CTGTTGAAGG TGCAGAAGGT CATGCAGAAG GTACCATTGA AACTGAAGAA

GATTCTATTC ATGTAGACTT TGAAGAATCG ACACATGAAA ATTCAAAACA

TCATGCTGAT GTTGTTGAAT ATGAAGAAGA TACAAACCCA GGTGGTGGTC

AGGTTACTAC TGAGTCTAAC CTAGTTGAAT TTGACGAAGA TTCTACAAAA

GGTATTGTAA CTGGTGCTGT TAGCGATCAT ACAACAATTG AAGATACGAA

AGAATATACG ACTGAAAGTA ACTTGATTGA ACTAGTAGAT GAACTACCTG

AAGAACATGG TCAAGCGCAA GGACCAATCG AGGAAATTAC TGAAAACAAT

CATCATATTT CTCATTCTGG TTTAGGAACT GAAAATGGTC ACGGTAATTA

TGGCGTGATT GAAGAAATCG AAGAAAATAG CCACGTGGAT ATTAAGAGTG

AATTAGGTTA CGAAGGTGGC CAAAATAGCG GTAATCAGTC ATTTGAGGAA

GACACAGAAG AAGATAAACC GAAATATGAA CAAGGTGGCA ATATCGTAGA

TATCGATTTC GATAGTGTAC CTCAAATTCA TGGTCAAAAT AATGGTAACC

AATCATTCGA AGAAGATACA GAGAAAGACA AACCTAAGTA TGAACAAGGT

GGTAATATCA TTGATATCGA CTTCGACAGT GTGCCACATA TTCACGGATT

CAATAAGCAC ACTGAAATTA TTGAAGAAGA TACAAATAAA GATAAACCAA

ATTATCAATT CGGTGGACAC AATAGTGTTG ACTTTGAAGA AGATACACTT

CCACAAGTAA GTGGTCATAA TGAAGGTCAA CAAACGATTG AAGAAGATAC

AACACCTCCA ATCGTGCCAC CAACGCCACC GACACCAGAA GTACCAAGCG

AGCCGGAAAC ACCAACACCA CCGACACCAG AAGTACCAAG CGAGCCGGAA

ACACCAACAC CGCCAACGCC AGAGGTACCA ACTGAACCTG GTAAACCAAT

ACCACCTGCT AAAGAAGAAC CTAAAAAACC TTCTAAACCA GTGGAACAAG

GTAAAGTAGT AACACCTGTT ATTGAAATCA ATGAAAAGGT TAAAGCAGTG

GTACCAACTA AAAAAGCACA ATCTAAGAAA TCTGAACTAC CTGAAACAGG

TGGAGAAGAA TCAACAAACA ACGGCATGTT GTTCGGCGGA TTATTTTAGCA

TTTTAGGTTTTAGCGTTATTA CGCAGAAATA AAAAGAATCA CAAAGCATAA

TCAATCCAAA ATTGACAGGT TTATTTCATA AATTATATGA AGTAAGCCTG
```

-continued
```
TTTTTTAAAA TTAAAACAAA TTTCCCAAGA AATAATTACA TACTCAATGA

CACTATGAAG GCGTTCTAAT TAGTGTTAAA ATGACGTTGA TACATAGATT

TAATACTTAG GAAAAGGAGC ACATTAACTT TGAAAAAAAT AAAAAAGGCA

ATCATTCCCG CTGCTGGTTT AGGGACTAGA TTTTTACCAG CAACTAAAGC

GATGCCAAAG GAAATGCTTC CTATCTTAGA TAAACCCACA ATACAATATA

TCGTTGAAGA AGCTGCAAGA GCTGGAATTG AAGATATTAT TATAGTGACA

GGTCGCCACA AACGCGCGAT TGAAGATCAT TTTGATAGTC AAAAAGAATT

AGAAATGGTG TTAAAAGAAA AAGGTAAATC TGAATTACTA GAGAAAGTTC

AGTATTCAAC GGAACTTGCG AATATTTTTT ATGTAAGGCA GAAAGAACAA

AAAGGTTTAG GGCATGC
``` whereby this nucleotide sequence encodes for the following protein starting at nucleotide no. 128 in the reading above, whereby the prepresent nucleotides are part of the signal system:

| | | | | |
|---|---|---|---|---|
| VKSNLRYGIR | KHKLGAASVF | LGTMIVVGMG | QEKEAAASEQ | NNTTVEESGS |
| SATESKASET | QTTTNNVNTI | DETQSYSATS | TEQPSQSTQV | TTEEAPKTVO |
| APKVETSRVD | LPSEKVADKE | TTGTQVDIAQ | QSKVSEIKPR | MKRSTDVTAV |
| AEKEVVEETK | ATGTDVTNKV | EVEEGSEIVG | HKQDTNVVNP | HNAERVTLKY |
| KWKFGEGIKA | GDYFDFTLSD | NVETHGISTL | RKVPEIKSTD | GQVMATGEII |
| GERKVRYTFK | EYVQEKKDLT | AELSLNLFID | PTTVTQKGNQ | NVEVKLGETT |
| VSKIFNIQYL | GGVRDNWGVT | ANGRIDTLNK | VDKFSHFAY | MKPNNQSLSS |
| VTVTGQVTKG | NKPGVNNPTV | KVYKHIGSDD | LAESVYAKLD | DVSKFEDVTD |
| NMSLDFDTNG | GYSLNFNNLD | QSKNYVIKYE | GYYDSNASNL | EFQTHLFGYY |
| NYYYTSNLTW | KNGVAFYSNN | AQGDGKDKLK | EPIIEHSTPI | ELEFKSEPPV |
| EKHELTGTIE | ESNDSKPIDF | EYHTAVEGAE | GHAEGTIETE | EDSIHVDFEE |
| STHENSKHHA | DVVEYEEDTN | PGGGQVTTES | NLVEFDEDST | KGIVTGAVSD |
| HTTIEDTKEY | TTESNLIELV | DELPEEHGQA | QGPIEEITEN | NHHISHSGLG |
| TENGHGNYGV | IEEIEENSHV | DIKSELGYEG | GQNSGNQSFE | EDTEEDKPKY |
| EQGGNIVDID | FDSVPQIHGQ | NNGNQSFEED | TEKDKPKYEQ | GGNIIDIDFD |
| SVPHIHGFNK | HTEIIEEDTN | KDKPNYQFGG | HNSVDFEEDT | LPQVSGHNEG |

| | | -continued | | |
|---|---|---|---|---|
| QQTIEEDTTP | PIVPPTPPTP | EVPSEPETPT | PPTPEVPSEP | ETPTPPTPEV |
| PTEPGKPIPP | AKEEPKKPSK | PVEQGKVVTP | VIEINEKVKA | VVPTKKAQSK |
| KSELPETGGE | ESTNNGMLFG | GLFSILGLAL | LRRNKKNHKA | |

In the single letter amino acid sequence above the following abbreviations have been used

| | |
|---|---|
| A | Ala, Alanine |
| R | Arg, Arginine |
| N | Asn, Asparagine |
| D | Asp, Aspartic acid |
| C | Cys, Cysteine |
| C | Cys, Cystine |
| G | Gly, Glycine |
| E | Glu, Glutamic acid |
| Q | Gln; Glutamine |
| H | His, Histidine |
| I | Ile, Isoleucine |
| L | Leu, Leucine |
| K | Lys, Lysine |
| M | Met, Methionine |
| F | Phe, Phenylalanine |
| P | Pro, Proline |
| S | Ser, Serine |
| T | Thr, Threonine |
| W | Trp, Tryptophan |
| Y | Tyr, Tyrosine |
| V | Val, Valine |

Above, the nucleotide sequence of the starting signal ends at nucleotide 235 and the sequence starting at nucleotide no. 1735 shows the nucleotide sequence of the binding region, which corresponds to the following amino acid sequence

| | | | | |
|---|---|---|---|---|
| IETEEDSIHV | DFEESTHHEN | SKHHADVVEY | EEDTNPGGGQ | VTTESNLVEF |
| DEDSTKGIVT | GAVSDHTTIE | DTKEYTTESN | LIELVDELPE | EHGQAQPIE |
| EITENNHHIS | HSGLGTENGH | GNYGVIEEIE | ENSHVDIKSE | LGYEGGQNSG |
| NQSFEEDTEE | DKPKYEQGGG | NIVDIDFDSV | PQIHGQNNGN | QSFEEDTEKD |
| KPKYEQGGNI | IDIDFDSVPH | IHGFNKHTEI | IEEDTNKDKP | NYQFGGHNSV |
| DFEEDTLPQV | SGHNEGQQTI | EEDTTPPIVP | PTPPTPEVPS | EPETPTPPTP |
| EVPSEPETPT | PPTPEVPTEP | GKPIPPAKEE | PKKPSKPVEQ | GKVVTPVIEI |
| NEKVKAVVPT | KKAQSKKSEL | PETGGESTN | NGMLFGGLFS | ILGLALLRRN | KKNHKA |

The invention further comprises a plasmid or phage comprising a nucleotide sequence coding for said fibronectin binding protein.

The invention further comprises a microorganism containing at least one hybrid-DNA-molecule according to the above. The plasmid pFR001 in an E. coli strain 259 has been deposited at the Deutsche Sammlung von Mikroorganismen (DSM), and has thereby been allocated the deposition number DSM 4124.

The invention further comprises a method for producing a fibronectin binding protein whereby at least one hybrid-DNA-molecule of above is transferred into a microorganism, cultivating said microorganism in a growth medium, and isolating the protein thus formed by means of affinity chromatography on a coloumn containing fibronectin bound to an insolubilized carrier followed by ion exchange chromatography.

A further aspect of the invention comprises a chemical synthesis of the fibronectin binding protein, whereby an amino acid sequence is built up based on said nucleotide sequence encoding for said protein starting from the C-terminal alanine which is stepwise reacted with the appropriate amino acid, whereby it is finally reacted with isoleucine at the N-terminal end, to form the fibronectin binding peptide region.

Appropriate carrier proteins can be coupled to the amino acid sequence as well, such as IgG binding regoins of protein A.

The invention will be described in the following with reference to the examples given, however, without being restricted thereto.

EXAMPLE

Chemical synthesis of a polypeptide based on the nucleotide sequence coding for the fibronectin binding domain was performed by building up the amino acid sequence corresponding to said nucleotide sequence starting from the C-terminal alanine and stepwise reacting with the appropriate amino acid and finally reacting with the isoleucine at the N-terminal end, in a solid phase synthesis according to the method by K. B. Merrifield, J. Am. Chem. Soc. 86, pp.304, (1964).

MATERIALS AND METHODS

Microorganism growth medium

For growth of E. coli bacteria the following medium was used. The amounts given relates to 1 litre of medium.

| | |
|---|---|
| Trypton Soy Broth (Oxoid Ltd, Basingstoke, Hants, GB) | 30 g |
| Yeast Extract (Oxoid) | 10 g |
| D-glucose | 40 g |
| $NH_4Cl$ | 2.5 g |
| $Na_2HPO_4.2H_2O$ | 7.5 g |
| $KH_2PO_4$ | 3.0 g |
| $Na_2SO_4.10H_2O$ | 2.5 g |
| $MgSO_4.7H_2O$ | 0.2 g |
| $CaCl_2.2H_2O$ | 0.5 mg |
| $FeCl_3.6H_2O$ | 16.7 mg |
| $ZnSO_4.7H_2O$ | 0.18 mg |
| $CuSO_4.5H_2O$ | 0.16 mg |
| $MnSO_4.4H_2O$ | 0.15 mg |
| $CoCl_2$ | 0.10 mg |
| NaEDTA | 20.1 mg |

Assay of fibronectin binding protein (FNBP)

Lysates of E. coli clones prepared in Tris-HCl buffer, containing lysozyme EDTA as earlier described (13), were analysed for fibronectin binding activity by measuring their ability to compete with staphylococcaL cells for binding the $^{125}$I-labelled 29 kD $NH_2$-terminal fragment of fibronectin. The amount of FNBP able to inhibit binding to 50% is considered as one unit of activity. Bovine fibronectin was provided by Dr. S. Johansson the Department of Medical and Physiological Chemistry, University of Uppsala, Sweden. Overnight cultures of E. coli were concentrated 10 times followed by lysis in 0.01M Tris-HCl, 0.001 EDTA, pH 7.9, 1 mg/ml of lysozyme. 100 μl lysate was mixed with 100 μl staphylococcal cells, 100 μl $^{125}$I bovinefibronectin (20000 cpm/ml), 200 μl PBS, and the mixture was incubated for 2 hrs at 20° C. After washing twice in PBS containing 0.1% BSA and 0.05% Tween the radioactivity of the mixture was measured in a gamma counter.

Iodinnation $^{125}$I-labelling of fibronectin and fibronectin fragments was performed using the chloramine-T method.

Bacterial strains and plasmids

E. coli TG-1 and DH-5alfa were used as bacterial hosts. The plasmid vectors were pBR322 and pUC18. Table 1 lists the plasmids.

Media and growth conditions

E. coli clones were grown in Luria Broth (LB) supplemented with ampicillin at 50 μg/ml and shaken at 37° C. The optical density was measured with a Linson 3,1 Photometer read at 540 nm. S. aureus was grown in Trypticase Soya Broth (TSB).

Restriction endonucleases and other enzymes

Restriction enzymes, T4 DNA ligase and Bal31 were purchased from Promega (Madison, Wis.), International Biotechnologies Inc. (New Haven, Conn.) and Boehringer Mannheim Biochemicals Scandinavia AB. Restriction mapping and fragment isolation were performed with $LiCl_4$ extracted plasmid DNA. Cloning in pUC18 was performed as described by Maniatis et al. Generation of subclones for sequencing was performed by ExoIII digestion using Erase-a-Base System purchased from Promega. E. coli clones were verified by restriction analysis, sequence analysis, and blot hybridazation. DNA sequencing was done by the dideoxy-nucleotide methods of Sanger et al, with the sequenase DNA sequencing kit purchased from United States Biochemical Corporation Cleveland Ohio, and the K/RT universal sequencing system purchased from Promega. The sequencing samples were analysed by wedge shaped gels using 6% polyacrylamide. Computer programms were used to record and analyse the sequence data.

The isolation of an E. coli clone containing gene 1 and part of gene 2 for a FNBP from S. aureus strain 8325-4 was described earlier. The plasmid pFR050 was constructed from S. aureus by cleaving 8325-4 chromosomal DNA with HindIII and XbaI. Fragments, 3–4 kbp in size were isolated after agarose-gel electrofores and ligated into pUC18. One clone containing fnbB sequences was isolated by colony hybridization using a synthetic oligonucleotide located downstream the HindIII-site in fnbB as a probe. The oligonucleotide was synthetized with Applied Biosystem 380A oligonucleotide synthetizer using the phosphoamidite method. Computer programms were used to record and analyse the sequence data.

Western blotting

Separated components were electroblotted onto NC-sheets (nitrocellulose sheets) (Schleicher and Schnell) for 2 hrs, 200 V using the miniblot system (LKB) and the buffer system described by Towbin. Subsequently NC-sheets were saturated with 1% BSA in TBS, pH 7.4, for 30 min, and incubated with 2.4 μg/ml bovine fibronectin in TBS, pH 7.4, for 2 hrs. After washing three times using PBS-Tween (0.1%), the NC-sheets were incubated with rabbit anti bovine fibronectin serum diluted 1:1000, which serum was a gift from Biochemical Centre, University of Uppsala, for 1.5 hrs, followed by washing and final incubation with a protein A peroxidase conjugate (prepared from S aureus A676 protein by conjugation with horse radish peroxidase (Boehringer) in a molar ratio of 1:2) for 1.5 hrs. After final washings 3 times with PBS-Tween, 1x with PBS, the blot was developed with 4-chloro-1-naphtol (Sigma).

Cloning of a gene coding for a second fibronectin binding protein

In our previous work it was described the cloning, expression and determination of the sequence of a gene coding for a fibronectin binding protein (gene 1). In a further analysis of these older sequence data it was found a region, located downstream of gene 1, which showed high homology with the beginning of gene 1. In order to determine if this region downstream of gene 1 exhibits a fibronectin binding activity, a 2.8 kb PstI fragment from pFR001 containing a sequence starting 680 bp downstream the stopcodon of gene 1 was introduced into the multilinker of pUC18. Knowing the transcription direction of gene 2 and its reading frame (from left to right in FIG. 1) it was possible to fuse the fragment in the correct reading frame to the lac-Z promoter of pUC18. This plasmid called pFR035, expressed fibronectin binding activity (Table 1 below). Thus there exist two different genes encoding FnBPs. However, when sequencing pFR035 it could not be found any stop codon in the inserted S. aureus DNA, and by comparing fnbA (gene 1) it was obvious that the complete fnbB was not present. By making southern blots of chromosomal DNA cleaved with HindIII alone, and together with other enzymes, we found that digestion with HindIII together with XbaI would generate a 3.5 kbp fragment (including 65 bp already present in pFR035), which most likely also would contain the missing 3'-part of fnbB. The fragment was cloned as described above and was called pFR050. Subclones of the plasmid were derived by digestion of pFR035 with ExoIII from the 3' end for different time periods with subsequent religation of the DNA, as described in Materials and Methods, above.

TABLE 1

Origin and expression of fibronectin binding activity for clones discussed in this invention. Assay for fibronectin binding is described in Materials and Methods, above.

| Clone | Derivation | Fn-binding |
| --- | --- | --- |
| pFR001 | Original isolate | + |
| pFR035 | 2.8 kb PstI fragment from pFR001 | + |
| pFR036 | 2.3 kb HpaI/EcoRI fragment from pFR001 | + |
| pFR035e31 | pFR035 with 1.3 kb deleted from the 3' PstI site (of which 1.1 kb is vector DNA) | – |
| pFR035e35 | as pFR035e31 but 1.47 kb deleted | – |
| pFR050 | Original isolate | + |
| pFR060 | 2.0 kbp NheI/SphI fragment from pFR050 inserted into pFR035 opened with NheI/SphI | + |

Sequence analysis

A nucleotide sequence of 1928 bp containing a domain encoding a fibronectin binding protein was determined by sequencing the overlapping subclones derived from pFR035 and pFR001 (FIG. 2). One open reading frame encodes a polypeptide of 940 amino acids, starting with a GTG codon at nucleotide 520, and terminating at the end of the clone at nucleotide 3342 (FIG. 2). FnbB, as fnbA (gene 1) has two possible initiation signals for transcription and a potential ribosome binding site (marked in FIG. 2). The start codon is followed by a possible signal sequence which shows 95% homology to that encoded by fnbA (FIG. 2, and 4). By comparison to FnBPA the cleavage site of the signal sequence is located between the second and third in row of three alanine residues. This corresponds to the cleavage site for the native protein isolated from S. aureus strain Newman. Downstream the signal sequence there is a stretch of about 66 amino acids with a 75% homology to the same stretch in fnbA. The following 444 amino acids have only 40% homology towards FnBPA and have several deletions/insertions, so the B-repeats found in FnBPA is not seen in FnBPB (FIGS. 2 and 4). However the reste of the peptide (394 aa) is nearly identical to FnBPA, the main difference being the deletion of 14 amino acids in FnBPB. This highly homologous region contains the same repeat (D1–D4 and Wr1–5) found in FnBPA with the exception that Wr1 is lacking. The Wc region and the hydrophobic region M domain as well as the mainly basic C-terminal end is conserved in FnBPB.

Expression of fibronectin binding protein and identification of the binding activity The E. coli clones pFR035 and pFR036 and subclones derived by deleting the gene 2 fragment of pFR035 were lysed and tested for fibronectin binding protein activity in the inhibition assay. Lysate of both clones inhibit $^{125}$I-labelled fibronectin to bind to S. aureus, whereas the subclone pFR035e31, deleted from the 3' terminal of the gene 2 fragment, has lost the activity (FIG. 3). The fibronectin binding protein activity is thus located to the amino acids downstream amino acid no. 535 (FIG. 1). None of these clones include the D-repeates which has been shown to be the only Fn-binding domain in FnBPA. This will imply that FnBPB contains two different Fn-binding domains one region upstream of amino acid 600 and the D-region.

Assay of the FnBp. E. coli clones containing different parts of the fnbB were analysed for Fn-binding activity by measuring their ability to compete with staphylococcal cells for binding of $^{125}$I-labelled intact bovine Fn or the 29 kDa N-terminal fragment. Over night cultures of E. coli were concentrated 10 times and lysed in 10 mM Tris-HCl, 1 mM EDTA, pH 7.9, 1 mg/ml lysozyme. 100 µl supernatant of centrifuged lysate was mixed with 100 µl staphylococcal cells ($5 \times 10^8$), 100 µL $^{125}$I-bovine Fn (20,000 cpm, 190 MBq/mg), 200 µl PBS and incubated 2 hrs at 20° C. After washing the mixture twice in PBS containing 0.1% BSA and 0.05 Tween$^R$ 20, the radioactivity bound to the bacterial cells was measured in a gamma counter.

Iodination, $^{125}$I-labelling of Fn and Fn fragments were done according to the chloramine-T method.

Molecular weight determination

Western blotting of lysate from pFR035 shows a band corresponding to a molecular weight of 100 kDa and several bands of lower molecular weight, which most likely are degradation products of the 100 kDa product since a shift to lower molecular weights is seen upon storage of the material. The difference seen in the processing is probably due to the fact that in pFR035 the FnBPB is fused to the beta-Gal protein, but in pFR036 it utilizes its own initiation signals, so the proteins are slightly different.

The data presented demonstrate that S. aureus has two different genes encoding for FnBPs. The start codon of fnbB is situated 682 bp downstream the stop codon of fnbA. This sequence between fnbA and fnbB contains a possible transcription termination signal located just a few bp downstream the said stop codon as well as transcription initiation signals located within the 90 bps which preceeds the start codon in fnbB. This implies that the genes are translated from different messenger RNAs. The region between these transcriptional signals does not contain any open reading frames preceeded by a ribosomal binding site on either strand. The 350 bp region upstream the romotor sequence of fnbB show strong homology with the analogous region of fnbA. In fnbA the binding activity has been localised to the D-repeate domain (between aa 745 and 872) near the cell wall associated part of the molecule, and a subclone where amino acids 746–1018 was excluded was Fn-binding negative. When the two genes are compared it is evident that there is no repeat region present in the pFR035 and pFR036. Still both express Fn-binding activity, which indicates that a non-homologous nucleotide sequence is present encoding for Fn-binding activity.

The expression of the fibronectin binding protein from gene 2 in E. coli, was lower than expression of gene 1.

The present fibronectin binding protein can be used for immunization, whereby the protein, preferably in combination with a fusion protein to create a large antigen to respond to, is injected in dosages causing immunological reaction in the host mammal. Thus the fibronectin binding protein can be used in vaccination of ruminants against mastitis caused by Staphylococcal infections.

Further, the fibronectin binding protein can be used to block an infection in an open skin wound by wound treatment using the fibronectin binding protein in a suspension. Thus the fibronectin binding protein can be used for the treatment of wounds, e.g. for blocking protein receptors, or for immunization (vaccination). In the latter case the host body produces specific antibodies, which can protect against invasion of bacterial strains comprising such a fibronectin binding protein. Hereby the antibodies block the adherence of the bacterial strains to damaged tissue.

Examples of colonizing of a tissue damage are:
a) colonizing of wounds in skin and connective tissue, which wounds have been caused by a mechanical trauma, chemical damage, and/or thermical damage;
b) colonizing of wounds on mucous membranes, such as in the mouth cavity, or in the mammary glands, urethra, or vagina;
c) colonizing on connective tissue proteins, which have been exposed by a minimal tissue damage (microlesion) in connection with epithelium and endothelium (mastitis, heart valve infection, hip exchange surgery).

When using the present FNBP, or the polypeptide, for the purpose of immunization (vaccination) in mammals, including man, the protein, or polypeptide is dispersed in sterile, isotonic saline solution, optionally while adding a pharmaceutically acceptable dispersing agent. Different types of adjuvants can further be used in order to sustain the release in the tissue, and thus expose the protein or the peptide for a longer time to the immundefense system of a body.

A suitable dosage to obtain immunization is 0,5 to 5 µg of FNBP, or polypeptide, per kg bodyweight and injection of immunization. In order to obtain a durable immunization, vaccination should be carried out at more than one consecutive occasions with an interval of 1 to 3 weeks, preferably at three occasions.

When using the present FNBP, or polypeptide, for topical, local administration the protein is dispersed in an isotonic saline solution to a concentration of 25 to 250 µg per ml. The wounds are then treated with such an amount only to obtain a complete wetting of the wound surface. For an average wound thus only a couple of millilitres of solution are used in this way. After treatment using the protein solution the wounds are suitably washed with isotonic saline or another suitable wound treatment solution.

Further the fibronectin binding protein as well as the minimal fibronectin binding site polypeptide, of the present invention can be used to diagnose bacterial infections caused by Staphylococci strains, whereby a fibronectin binding protein of the present invention is immobilized on a solid carrier, such as small latex or Sepharose$^R$ beads, whereupon sera containing antibodies are allowed to pass and react with the FNBP thus immobilized. The agglutination is then measured by known methods.

Further, the FNBP, or the polypeptide can be used in an ELISA test (Enzyme Linked Immuno Sorbent Assay; E Engvall, Med. Biol. 55, 193, (1977)). Hereby wells in a polystyrene microtitre plate are coated with the FNBP, and incubated over night at 4° C. The plates are then thoroughly washed using PBS containing 0.05% TWEEN 20, and dried. Serial dilution of the patient serum were made in PBS-Tween, were added to the wells, and incubated at 30° C. for 1.5 hrs. After rinsing antihuman-IgG conjugated with an enzyme, or an antibovine-IgG conjugated with an enzyme, respectively, horseradishperoxidase or an alkaline phosphatase, was added to the wells and incubated at 30° C. for 1,5 hrs, whereupon when the IgG has been bound thereto, and after rinsing, an enzyme substrate is added, a p-nitrophosphate in case of an alkaline phosphatase, or ortophenylene diamine substrate (OPD) in case a peroxidase has been used, respectively. The plates comprising the wells were thus then rinsed using a citrate buffer containing 0.055% OPD, and 0.005% $H_2O_2$, and incubated at 30° C. for 10 min. Enzyme reaction was stopped by adding a 4N solution of $H_2SO_4$ to each well. The colour development was measured using a spectrophotometer.

Depending on the type of enzyme substrate used a fluoroscense measurement can be used as well.

Another method to diagnose Staphylococci infections is by using the DNA gene probe method based on the FNBP sequence or the polypeptide sequence. Thereby the natural or synthetic DNA sequences are attached to a solid carrier, such as a polystyrene plate as mentioned above, by e.g. adding a milk in the case of diagnozing a mastitis, to the surface. The DNA gene probe, optionally labelled enzymatically, or by a radioactive isotope is then added to the solid surface plate comprising the DNA sequence, whereby the DNA gene probe attaches to the sequence where appearing. The enzyme or the radioactive isotope can then readily be determined by known methods.

Above the term fibronectin binding protein includes the polypeptide sequence as well, which polypeptide sequence forms the minimal fibronectin binding site of the complete protein.

REFERENCES

8. Beachey, E. H. and Simpson, W. A(1982). Infection 10, 107–110.
9. Courtney, H. S., Ofek, I., Simpson, W. A., Hasty, D. L. and Beachey, E. H. (1986). Infect. Immun. 53, 454–459.
11. Espersen, F. and Clemmensen, I. (1982). Infect. Immun. 37, 526–531.
12. Fröman, G., Switalski, L. M., Speziale, P. and Hook, M. (1987). J. Biol. Chem. 262, 2564–2571
1. Hynes, R. O. (1985) Annu. Rev. Cell Biol. 1, 67–90.
2. Hynes, R. O. (1986) Sci. Ann. 254, 42–51.
6. Kuusela, P. (1978) Nature 276, 718–720.
13. Löfdahl, S., Guss B., Uhlén, M., Philipson, L. and Lindberg, M. (1983) Proc. Natl. Acad. Sci. USA 80, 697–701.
3. Ruoslahti, E. and Pierschbacher, M. D. (1986). Cell, 44, 517–518.
10. Rydén, C., Rubin, K., Speziale, P., Höök, M., Lindberg, M. and Wadström, T. (1983), J. Biol. Chem. 258, 3396–3401.
4. Woods, A., Couchman, J. R., Johansson, S., and Höök, M. (1986), EMBO J. 5, 665–670.
5. Yamada, K. M. (1983), Annu. Rev. Biochem. 52, 761–799.

LEGENDS TO THE FIGURES

FIG. 1 Sequence of the nucleotide encoding for the fibronectin binding protein

The nucelotide sequence for the fibronectin binding protein is given.

FIG. 2. Comparison between amino acid sequences

The amino acid sequences of gene 1 and gene 2, repsectively, are given in parallel.

FIG. 3. Restriction map (A) Restriction map of the original clones pFR0001 and pFR050 together with subclones pFR035 and pFR036. The location of fnbA and fnbB is indicated. The sequenced fragment of the insert is shown in more detail. The coding sequence in each clone are shown with bold lines.

FIG. 4. Deduced amino acid sequence of the cloned fnbB from S. aureus strain 8325-4.

Figure 5:
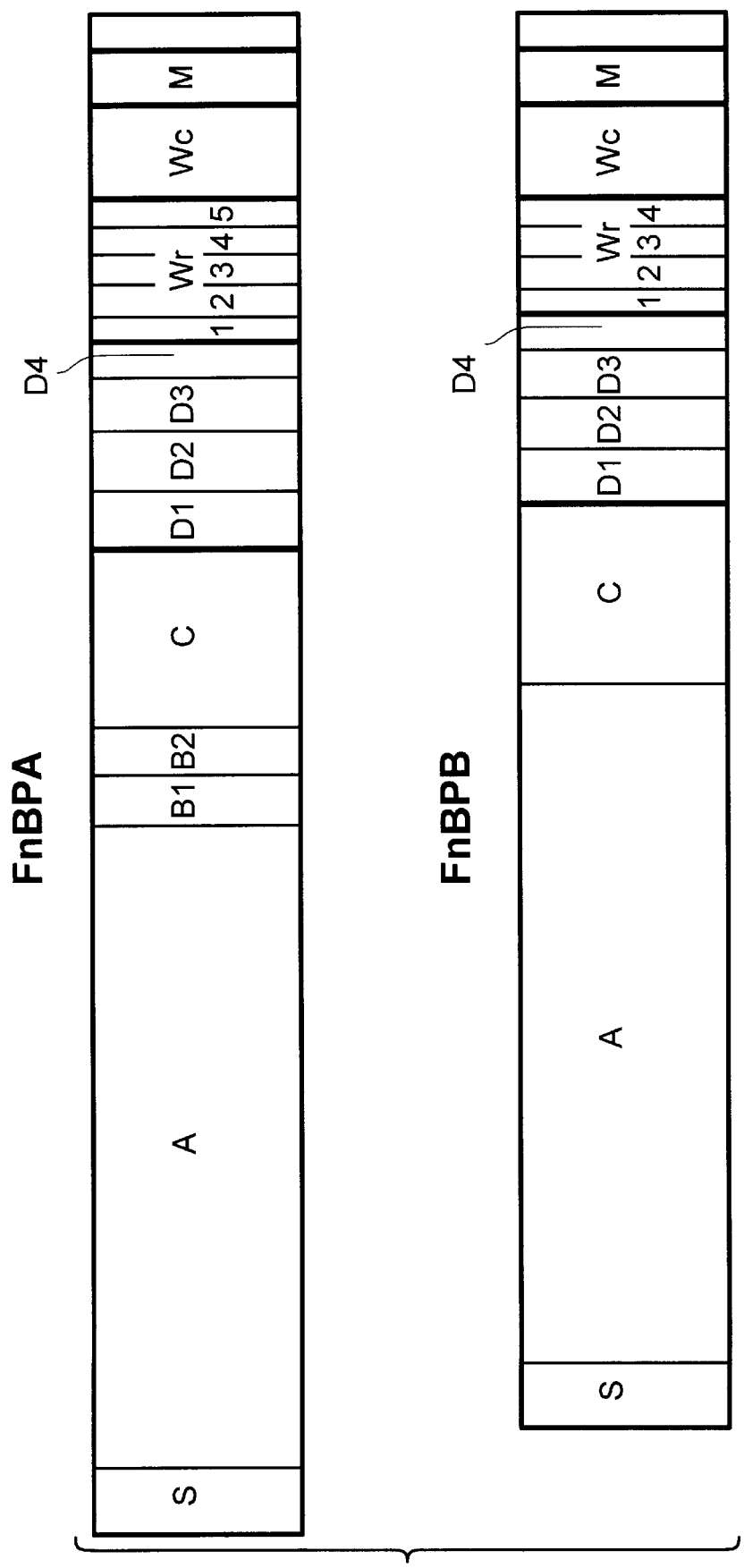
FIG. 5 is a schematic drawing comparing domain organization of FnBPA and FnBPB.

FIG. 5. Schematic drawing comparing domain organization of FnBPA and FnBPB.

We claim:

1. A protein having fibronectin binding activity, wherein said protein is encoded by a hybrid DNA molecule from Staphylococcus aureus wherein the hybrid DNA molecule consists of the following nucleotide sequence:

GTTAACAACA ATCTTAACTT TTTATTAACT

CGCTTTTTTT CATTGCTTTT

AAAAACCGAA CAATATAGAA TTGCATTTAT

```
                        TGAGTTTTTA AAATAAATGA

ATTTTGCATT TAAGGGAGAA TATTATAGTG

AAAAGCAATC TTAGATACGG

CATAAGAAAA CACAAATTGG GAGCGGCCTC

AGTATTCTTA GGAACAATGA

TCGTTGTTGG AATGGGACAA GAAAAAGAAG

CTGCAGCATC GGAACAAAAC

AATACTACAG TAGAGGAAAG TGGGAGTTCA

GCTACTGAAA GTAAAGCAAG

CGAAACACAA ACAACTACAA ATAACGTTAA

TACAATAGAT GAAACACAAT

CATACAGCGC GACATCAACT GAGCAACCAT

CACAATCAAC ACAAGTAACA

ACAGAAGAAG CACCGAAAAC TGTGCAAGCA

CCAAAAGTAG AAACTTCGCG

AGTTGATTTG CCATCGGAAA AAGTTGCTGA

TAAGGAAACT ACAGGAACTC

AAGTTGACAT AGCTCAACAA AGTAAAGTCT

CAGAAATTAA ACCAAGAATG

AAAAGATCAA CTGACGTTAC AGCAGTTGCA

GAGAAAGAAG TAGTGGAAGA

AACTAAAGCG ACAGGTACAG ATGTAACAAA

TAAAGTGGAA GTAGAAGAAG

GTAGTGAAAT TGTAGGACAT AAACAAGATA

CGAATGTTGT AAATCCTCAT

AACGCAGAAA GAGTAACCTT GAAATATAAA

TGGAAATTTG GAGAAGGAAT

TAAGGCGGGA GATTATTTTG ATTTCACATT
```

```
                        AAGCGATAAT GTTGAAACTC

ATGGTATCTC AACACTGCGT AAAGTTCCGG

AGATAAAAAG TACAGATGGT

CAAGTTATGG CGACAGGAGA AATAATTGGA

GAAAGAAAAG TTAGATATAC

GTTTAAAGAA TATGTACAAG AAAAGAAAGA

TTTAACTGCT GAATTATCTT

TAAATCTATT TATTGATCCT ACAACAGTGA

CGCAAAAAGG TAACCAAAAT

GTTGAAGTTA AATTGGGTGA GACTACGGTT

AGCAAAATAT TTAATATTCA

ATATTTAGGT GGAGTTAGAG ATAATTGGGG

AGTAACAGCT AATGGTCGAA

TTGATACTTT AAATAAAGTA GATGGGAAAT

TTAGTCATTT TGCGTACATG

AAACCTAACA ACCAGTCGTT AAGCTCTGTG

ACAGTAACTG GTCAAGTAAC

TAAAGGAAAT AAACCAGGGG TTAATAATCC

AACAGTTAAG GTATATAAAC

ACATTGGTTC AGACGATTTA GCTGAAAGCG

TATATGCAAA GCTTGATGAT

GTCAGCAAAT TTGAAGATGT GACTGATAAT

ATGAGTTTAG ATTTTGATAC

TAATGGTGGT TATTCTTTAA ACTTTAATAA

TTTAGACCAA AGTAAAAATT

ATGTAATAAA ATATGAAGGG TATTATGATT

CAAATGCTAG CAACTTAGAA

TTTCAAACAC ACCTTTTGG ATATTATAAC
```

19

-continued

```
                              TATTATTATA CAAGTAATTT
AACTTGGAAA AATGGCGTTG CATTTTACTC
                              TAATAACGCT CAAGGCGACG
GCAAAGATAA ACTAAAGGAA CCTATTATAG
                              AACATAGTAC TCCTATCGAA
CTTGAATTTA AATCAGAGCC GCCAGTGGAG
                              AAGCATGAAT TGACTGGTAC
AATCGAAGAA AGTAATGATT CTAAGCCAAT
                              TGATTTTGAA TATCATACAG
CTGTTGAAGG TGCAGAAGGT CATGCAGAAG
                              GTACCATTGA AACTGAAGAA
GATTCTATTC ATGTAGACTT TGAAGAATCG
                              ACACATGAAA ATTCAAAACA
TCATGCTGAT GTTGTTGAAT ATGAAGAAGA
                              TACAAACCCA GGTGGTGGTC
AGGTTACTAC TGAGTCTAAC CTAGTTGAAT
                              TTGACGAAGA TTCTACAAAA
GGTATTGTAA CTGGTGCTGT TAGCGATCAT
                              ACAACAATTG AAGATACGAA
AGAATATACG ACTGAAAGTA ACTTGATTGA
                              ACTAGTAGAT GAACTACCTG
AAGAACATGG TCAAGCGCAA GGACCAATCG
                              AGGAAATTAC TGAAAACAAT
CATCATATTT CTCATTCTGG TTTAGGAACT
                              GAAAATGGTC ACGGTAATTA
TGGCGTGATT GAAGAAATCG AAGAAAATAG
                              CCACGTGGAT ATTAAGAGTG
AATTAGGTTA CGAAGGTGGC CAAAATAGCG
```

20

-continued

```
                              GTAATCAGTC ATTTGAGGAA
GACACAGAAG AAGATAAACC GAAATATGAA
                              CAAGGTGGCA ATATCGTAGA
TATCGATTTC GATAGTGTAC CTCAAATTCA
                              TGGTCAAAAT AATGGTAACC
AATCATTCGA AGAAGATACA GAGAAAGACA
                              AACCTAAGTA TGAACAAGGT
GGTAATATCA TTGATATCGA CTTCGACAGT
                              GTGCCACATA TTCACGGATT
CAATAAGCAC ACTGAAATTA TTGAAGAAGA
                              TACAAATAAA GATAAACCAA
ATTATCAATT CGGTGGACAC AATAGTGTTG
                              ACTTTGAAGA AGATACACTT
CCACAAGTAA GTGGTCATAA TGAAGGTCAA
                              CAAACGATTG AAGAAGATAC
AACACCTCCA ATCGTGCCAC CAACGCCACC
                              GACACCAGAA GTACCAAGCG
AGCCGGAAAC ACCAACACCA CCGACACCAG
                              AAGTACCAAG CGAGCCGGAA
ACACCAACAC CGCCAACGCC AGAGGTACCA
                              ACTGAACCTG GTAAACCAAT
ACCACCTGCT AAAGAAGAAC CTAAAAAACC
                              TTCTAAACCA GTGGAACAAG
GTAAAGTAGT AACACCTGTT ATTGAAATCA
                              ATGAAAAGGT TAAAGCAGTG
GTACCAACTA AAAAAGCACA ATCTAAGAAA
                              TCTGAACTAC CTGAAACAGG
TGGAGAAGAA TCAACAAACA ACGGCATGTT
```

-continued

```
                    GTTCGGCGGA  TTATTTAGCA

TTTTAGGTTT  AGCGTTATTA  CGCAGAAATA

AAAAGAATCA  CAAAGCATAA

TCAATCCAAA  ATTGACAGGT  TTATTTCATA

AATTATATGA  AGTAAGCCTG

TTTTTTAAAA  TTAAAACAAA  TTTCCCAAGA

AATAATTACA  TACTCAATGA

CACTATGAAG  GCGTTCTAAT  TAGTGTTAAA

ATGACGTTGA  TACATAGATT

TAATACTTAG  GAAAAGGAGC  ACATTAACTT

TGAAAAAAAT  AAAAAAGGCA

ATCATTCCCG  CTGCTGGTTT  AGGGACTAGA

TTTTTACCAG  CAACTAAAGC

GATGCCAAAG  GAAATGCTTC  CTATCTTAGA

TAAACCCACA  ATACAATATA
```

-continued

```
TCGTTGAAGA  AGCTGCAAGA  GCTGGAATTG

AAGATATTAT  TATAGTGACA

GGTCGCCACA  AACGCGCGAT  TGAAGATCAT

TTTGATAGTC  AAAAAGAATT

AGAAATGGTG  TTAAAAGAAA  AAGGTAAATC

TGAATTACTA  GAGAAAGTTC

AGTATTCAAC  GGAACTTGCG  AATATTTTTT

ATGTAAGGCA  GAAAGAACAA

AAAGGTTTAG  GCATGC
``` wherein said protein is produced by a process comprising the steps of a) cloning said hybrid DNA molecule into a microorganism such that said DNA is expressed by said microorganism;

b) cultivating the microorganism in a growth promoting medium; and c) lysing the cloned microorganism.

2. A protein from *Staphylococcus aureus* having fibronectin binding activity wherein the protein consists of one amino acid sequence selected from the group consisting of:

```
VKSNLRYGIR  KHKLGAASVF  LGTMIVVGMG  QEKEAAASEQ  NNTTVEESGS

SATESKASET  QTTTNNVNTI  DETQSYSATS  TEQPSQSTQV  TTEEAPKTVO

APKVETSRVD  LPSEKVADKE  TTGTQVDIAQ  QSKVSEIKPR  MKRSTDVTAV

AEKEVVEETK  ATGTDVTNKV  EVEEGSERVG  JKQDTNVVNP  HNAERVTLKY

KWKFGEGIKA  GDYFDFTLSD  NVETHGISTL  RKVPEIKSTD  GQVMATGEII

GERKVRYTFK  EYVQEKKDLT  AELSLNLFID  PTTVTQGNQ   NVEVKLGETT

VSKIFNIQYL  GGVRDNWGVT  ANGRIDTLNK  VDGKFSHFAY  MKPNNQSLSS

VTVTGQVTKG  NKPGVNNPTV  KVYKHIGSDD  LAESVYAKLD  DVSKFEDVTD

NMSLDFDTNG  GYSLNFNNLD  QSKNYVIKYE  GYYDSNASNL  EFQTHLFGYY

NYYYTSNLTW  KNGVAFYSNN  AQGDGKDKLK  EPIIEHSTPI  ELEFKSEPPV

EKHELTGTIE  ESNDSKPIDF  EYHTAVEGAE  GHAEGTIETE  EDSIHVDFEE

STHENSKHHA  DVVEYEEDTN  PGGGQVTTES  NLVEFDEDST  KGIVTGAVSD
```

| | | | | |
|---|---|---|---|---|
| HTTIEDTKEY | TTESNLIELV | DELPEEGHQA | QGPIEEITEN | NHHISHSGLG |
| TENGHGNYGV | IEEIEENSHV | DIKSELGYEG | GQNSGNQSFE | EDTEEDKPKY |
| EQGGNIVDID | FDSVPQIHGQ | NNGNQSFEED | TEKDKPKYEQ | GGNIIDIDFD |
| SVPHIHGFNK | HTEIIEEDTN | KNKPNYQFGG | HNSVDFEEDT | LPQVSGHNEG |
| QQTIEEDTTP | PIVPPTPPTP | EVPSEPETPT | PPTPEVPSEP | ETPTPPTPEV |
| PTEPGKPIPP | AKEEPKKPSK | PVEQGKVVTP | VIEINEKVKA | VVPTKKAQSK |
| KSELPETGGE | ESTNNGMLFG | GLVSILGLAL | LRRNKKNHKA | | and

| | | | | |
|---|---|---|---|---|
| IETEEDSIHV | DFEESTHHEN | SKHHADVVEY | EEDTNPGGGQ | VTTESNLVEF |
| DEDSTKGIVT | GAVSDHTTIE | DTKEYTESN | LIELVDELPE | EHGQAQGPIE |
| EITENNHHIS | HSGLGTENGH | GNYGVIEEIE | ENSHVDIKSE | LGYEGGQNSG |
| NQSFEEDTEE | DKPKYEQGGG | NIVDIDFDSV | PQIHGQNNGN | QSFEEDTEKD |
| KPKYEQGGNI | IDIDFDSVPH | IHGFNKHTEI | IEEDTNKNKP | NYQFGGHNSV |
| DFEEDTLPQV | SGHNEGQQTI | EEDTTPPIVP | PTPPTPEVPS | EPETPTPPTP |
| EVPSEPETPT | PPTPEVPTEP | GKPIPPAKEE | PKKPSKPVEQ | GKVVTPVIEI |
| NEKVKAVVPT | KKAQSKKSEL | PETGGEESTN | NGMLFGGLVS | ILGLALLRRN | KKNHKA | wherein said protein is produced by a process comprising the steps of
  a) cloning at least one hybrid DNA molecule encoding said protein into a microorganism such that said DNA is expressed by said microorganism;
  b) cultivating the microorganism in a growth promoting medium; and
  c) lysing the cloned microorganism.

3. A composition comprising a protein according to claim 2 and a carrier exogenous to *Staphylococcus aureus*.

4. A composition comprising a protein according to claim 2 and a carrier therefor.

5. A fusion protein comprising a protein according to claim 2.

6. A fusion protein comprising a protein according to claim 1.

7. A protein according to claim 1, wherein said microorganism is *E. coli*.

8. A protein according to claim 2, wherein said microorganism is *E. coli*.

* * * * *

UNITED STATES PATENT AND TRADEMARK OFFICE
CERTIFICATE OF CORRECTION

PATENT NO.   : 5,840,846
DATED        : November 24, 1998
INVENTOR(S)  : Magnus Hook et al.

It is certified that error appears in the above-identified patent and that said Letters Patent is hereby corrected as shown below:

Figure 4,
Please delete amino acid 100 "O" and insert -- Q -- such that amino acids 91-100 read as -- TTEEAPKTVQ --.

Columns 7-8,
In the amino acid sequence, please delete the last set of amino acid in the second row "TTEEAPKTVO" and insert -- TTEEAPKTVQ --.

Claim 2,
In the amino acid sequence, please delete the last set of amino acid in the second row "TTEEAPKTVO" and insert -- TTEEAPKTVQ --.

Columns 9-10,
In the amino acid sequence, between lines 35 and 58, please delete "DFEESTHHEN" and the first row and second column of the amino acid sequence and insert
-- DFEESTHEN --.
In the amino acid sequence, between lines 35 and 58, please delete "DKPKYEQGGG" in the fourth row and second column of the amino acid sequence and insert
-- DKPKYEQGG --.
In the amino acid sequence, between lines 35 and 58, please delete "PETGGESTN" in the eighth row and third column of the amino acid sequence and insert
-- PETGGEESTN --.

Claim 2,
In the amino acid sequence, please delete "DELPEEGHQA" in the first row and third column of the amino acid sequence and insert -- DELPEEHGQA --.
In the amino acid sequence, please delete "KNKPNYQFGG" in the fourth row and third column of the amino acid sequence and insert -- KDKPNYQFGG --.
In the amino acid sequence, please delete "GLVSILGLAL" in the seventh row and third column of the amino acid sequence and insert -- GLFSILGLAL --.
In the amino acid sequence, please delete "DFEESTHHEN" in the eighth row and second column of the amino acid sequence and insert -- DFEESTHEN --.
In the amino acid sequence, please delete "DTKEYTESN" in the ninth row and third column of the amino acid sequence and insert -- DTKEYTTESN --.
In the amino acid sequence, please delete "DKPKYEQGGG" in the eleventh row and second column of the amino acid sequence and insert -- DKPKYEQGG --.

UNITED STATES PATENT AND TRADEMARK OFFICE
CERTIFICATE OF CORRECTION

PATENT NO. : 5,840,846
DATED : November 24, 1998
INVENTOR(S) : Magnus Hook et al.

It is certified that error appears in the above-identified patent and that said Letters Patent is hereby corrected as shown below:

Claim 2 (continued),
In the amino acid sequence, please delete "IEEDTNKNKP" in the twelfth row and fourth column of the amino acid sequence and insert -- IEEDTNKDKP --.
In the amino acid sequence, please delete "NGMLFGGLVS" in the last row and fourth column of the amino acid sequence and insert -- NGMLFGGLFS --.

Signed and Sealed this

Twenty-second Day of January, 2002

Attest:

Attesting Officer

JAMES E. ROGAN
Director of the United States Patent and Trademark Office